United States Patent [19]

Bourke

[11] Patent Number: 5,536,168

[45] Date of Patent: *Jul. 16, 1996

[54] MOUTH WORN APPARATUS, A METHOD FOR TREATING JAW AND TEETH MALFORMATIONS, AND A METHOD FOR PREVENTING SNORING

[76] Inventor: Kevin J. Bourke, 1 High Street, East Maitland, NSW, Australia, 2320

[*] Notice: The term of this patent shall not extend beyond the expiration date of Pat. No. 5,163,840.

[21] Appl. No.: 347,881

[22] Filed: Nov. 30, 1994

Related U.S. Application Data

[63] Continuation of Ser. No. 154,782, Nov. 17, 1993, abandoned.

[51] Int. Cl.⁶ .................................................. A61C 3/00
[52] U.S. Cl. ................................. 433/6; 433/7; 433/24
[58] Field of Search ............................ 433/6, 7, 18, 229; 601/139, 164; 128/861, 859, 848

[56] References Cited

U.S. PATENT DOCUMENTS 2,257,709  9/1941  Anderson .
3,874,084  4/1975  Cole ........................................ 601/164
4,591,341  5/1986  Andrews .
4,919,612  4/1990  Bergersen ................................. 433/6
5,163,840  11/1992  Bourke ..................................... 433/6
5,259,762  11/1993  Farrell ..................................... 433/6

FOREIGN PATENT DOCUMENTS

0886254  11/1971  Canada ................................. 128/861

Primary Examiner—Cary E. O'Connor
Attorney, Agent, or Firm—Darby & Darby

[57] ABSTRACT

A mouth worn apparatus is disclosed which includes a main body having upper and lower compartments which are generally U-shaped so as to conform generally to a patient's teeth, the upper compartment opening at least upwardly and the lower compartment opening at least downwardly so as to generally receive a patient's upper and lower teeth. A plurality of flexible protrusion members extend from at least part of the interior surface of at least one of the compartments so as to contact at least some of the patient's teeth when the device is worn. The device is used by placing it in the patient's mouth so that the upper and lower teeth are received in the upper and lower compartments respectively and retaining the device in the patient's mouth for a prescribed period of time.

17 Claims, 6 Drawing Sheets

MOUTH WORN APPARATUS, A METHOD FOR TREATING JAW AND TEETH MALFORMATIONS, AND A METHOD FOR PREVENTING SNORING

This is a continuation of application Ser. No. 8/154,782, filed Nov. 17, 1993 abandoned.

FIELD OF THE INVENTION

This invention is directed to the field of human and animal health and, in particular, concerns medico/dental methods of treatment whereby unsatisfactory physical conditions can be ameliorated and well-being promoted. The invention also includes within its ambit an improved device for carrying out such methods.

BACKGROUND OF THE INVENTION

In the Inventor's U.S. Pat. No. 5,163,840, there is proposed a method for treating jaw and tooth malformation. This method is directed at moving one or more of the patient's teeth. An apparatus for treating the jaw and tooth malformation is also proposed. The apparatus is preferably made of a soft, resilient material, having upper and lower compartments which are generally U-shaped so as to receive a patient's teeth, each compartment having side walls and a connecting wall joining the side walls, and a plurality of flexible protrusion members. The flexible protrusion members extend from the walls into the interior compartment so as to contact the patient's teeth when the device is worn. Once the appropriate device is selected, the device is then placed in the mouth of the patient so that the upper and lower teeth are received in the upper and lower compartments of the device respectively, and then the device is retained within the patient's mouth for a predetermined period of time during a substantial portion of which the patient is at rest.

Whilst the aforementioned device provides many differences and advantages over the prior art, the inventor has now discovered that certain other variations and modifications can be made to the device which allow a more efficient use of the device for the treatment of jaw and tooth malformations. The inventor has also discovered that the device is not only useful for treating jaw and tooth malformations, but due to the unique configuration of the device, it is also useful, worn nocturnally, as an anti-snoring device, or as an orthodontic retainer.

In one aspect, the invention provides a mouth worn apparatus, comprising:
- a main body having upper and lower compartments which are generally U-shaped so as to conform generally to a patient's teeth, the upper compartment opening at least upwardly and the lower compartment opening at least downwardly so as to generally receive a patient's upper and lower teeth, respectively; and,
- a plurality of flexible protrusion members extending from at least part of the interior surface of at least one of said compartments so as to contact at least some of the patient's teeth when the device is worn.

Preferably, certain of said protrusion members being positioned to contact certain parts of selected teeth are longer in comparison to those positioned to contact other of said teeth.

In use, gradual movement of said teeth is facilitated when said apparatus is worn by a patient.

In one form of the invention wherein each said compartment comprised at least one side wall and a connecting wall.

In a further form of the invention, each compartment comprises a pair of side walls and a connecting wall.

In a preferred embodiment, certain portions of said side wall(s) are selectively removed.

In a further preferred embodiment certain portions of said side wall(s) are provided with one or more vertical cut(s) therein.

A preferred use of the device is when it is used as an anti-snoring device.

A preferred use of the device is also for the prevention of clenching or bruxing of the patient's teeth.

A still further preferred use of the device is as an orthodontic retainer.

In a further aspect, the present invention provides a method for treating jaw and tooth malformations, said method being directed at moving one or more of a patient's teeth and making use of an apparatus having upper and lower compartments which are generally U-shaped so as to conform generally to a patient's teeth, and having a plurality of flexible protrusion members extending from at least part of the interior surface of at least one of said compartments so as to contact at least some of the patient's teeth when the device is worn, said method comprising the steps of:
- selectively cutting away portions of said protrusion members and/or the wall portions of said compartment(s), and/or providing one or more vertical cut(s) in the wall portions of said compartment(s);
- placing the device in the mouth of a patient so that the upper and lower teeth are substantially received in the upper and lower compartments of the device, respectively, and,
- retaining the device within the patient's mouth for a predetermined period of time such that any protrusion members which contact the patient's teeth apply pressure thereto whereby gradual movement of said teeth is facilitated.

In yet a further aspect, the present invention provides a method for preventing snoring and/or clenching or bruxing of the teeth, said method making use of an apparatus having upper and lower compartments which are generally U-shaped so as to conform generally to a person's teeth, and having a plurality of flexible protrusion members extending from at least part of the interior surface of at least one of said compartments so as to contact at least some of the patient's teeth when the device is worn, said method comprising the steps of:
- selecting a device in which the compartments generally conform to a person's teeth;
- placing device in the person's mouth so that the upper and lower teeth are received in the upper and lower compartments of the device respectively; and,
- retaining the device in the person's mouth nocturnally, such that the mandible is brought downward and forward to thereby prevent snoring.

BRIEF DESCRIPTION OF THE DRAWINGS

The foregoing brief description as well as various objects, features and advantages of the present invention will be understood more completely from the following detailed description of a presently preferred but nonetheless illustrative embodiments, of the invention with reference being had to the accompanying drawings in which.

DETAILED DESCRIPTION OF THE PREFERRED EMBODIMENTS

Throughout the description, like numerals are utilized to represent similar features. A full description of the device and its method of use will be found in the Applicant/Inventor's earlier U.S. Pat. No. 5,163,840, the entire disclosure of which are now incorporated herein by referenced thereto. As shown in the drawings, the device 10 is adapted to be comfortably and safely positioned within the mouth of a user in the general manner of a sporting person's mouthpiece or mouth guard. It is suitably of unitary one-piece construction, made of soft flexible rubber of the type employed in the manufacture of nipples for baby bottles. Alternatively, it can be made from a suitable inert plastic or silicone (a)-based material.

Figure 1A:
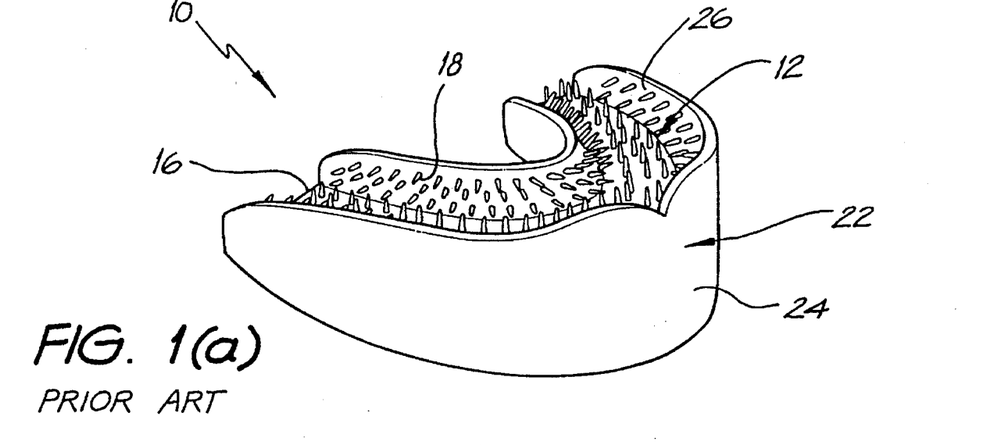
FIGS. 1(a), 1(b) and 1(c) illustrate, respectively, perspective, plan and front views of the device illustrated in the Applicant's earlier U.S. Pat. No. 5,163,840.
Figure 1B:
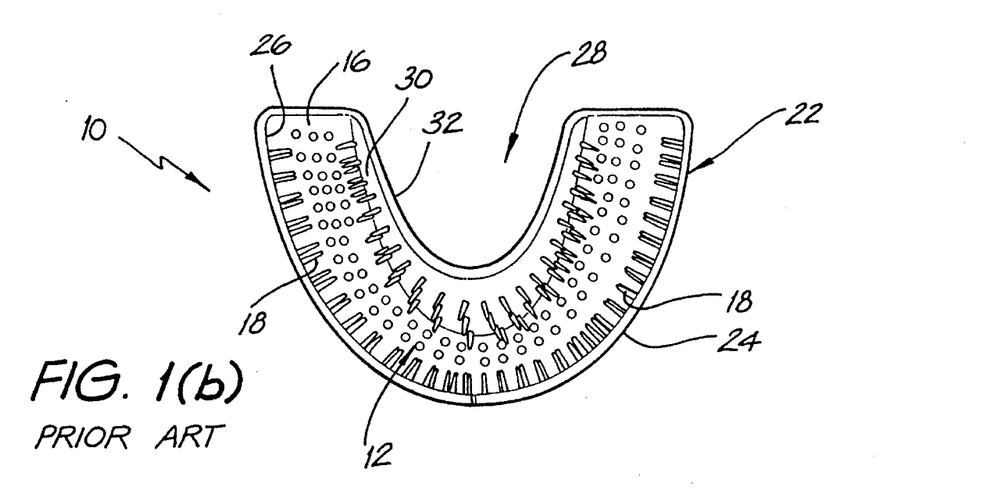
Figure 1C:
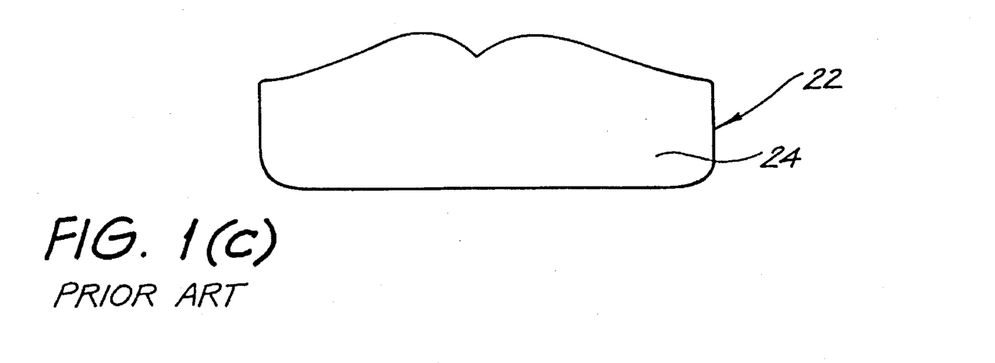
Figure 2A:
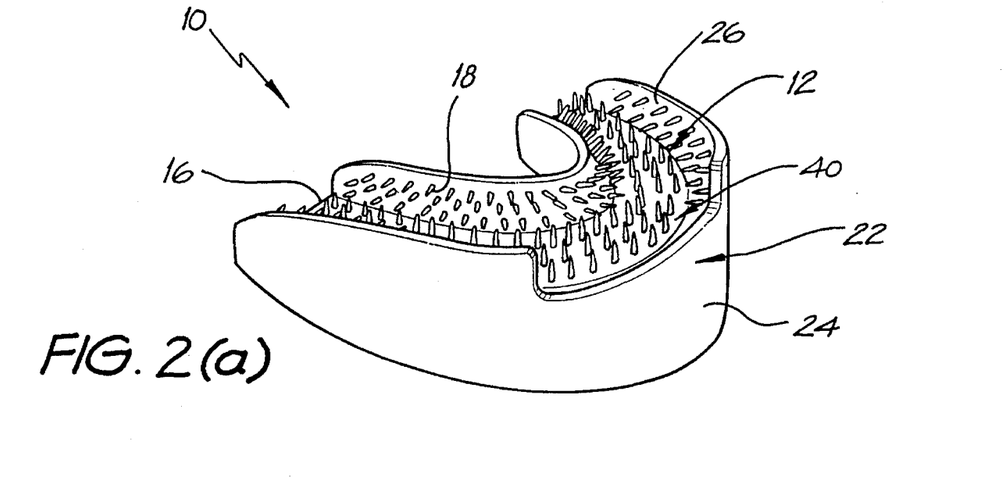
FIGS. 2(a), 2(b) and 2(c) illustrate, respectively, perspective, plan and front views of the device in accordance with one aspect of the present invention whereby a portion of a side wall is cut out.
Figure 2B:
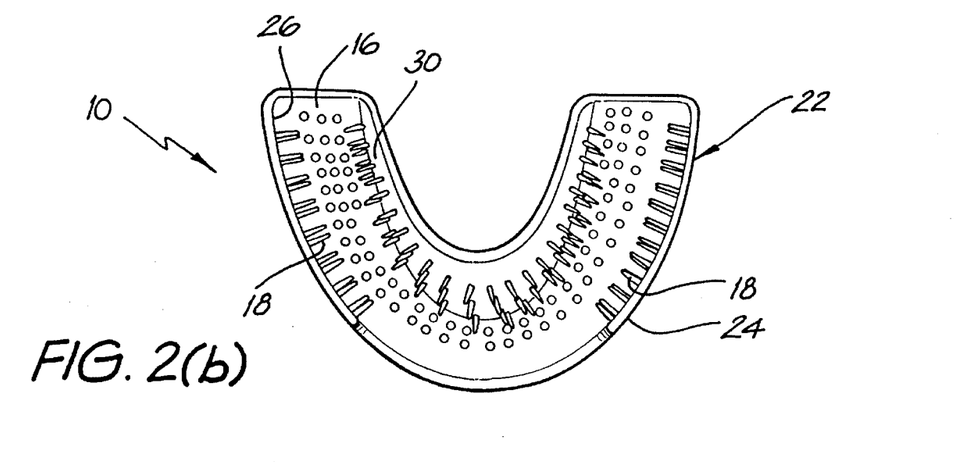
Figure 2C:
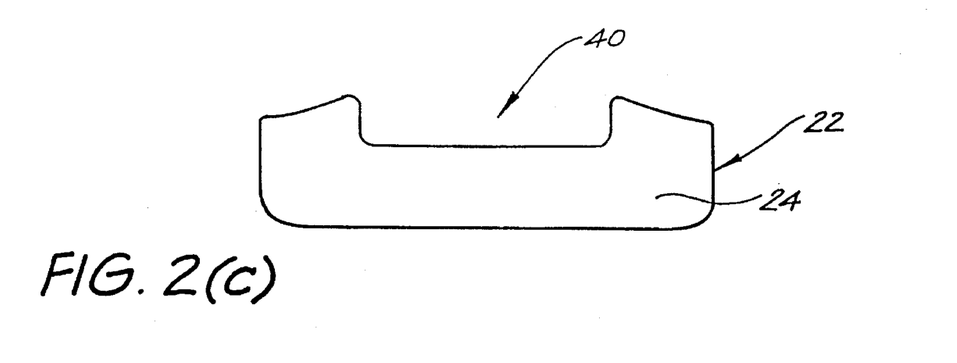

Examined in further detail, the device 10, viewed from directly above, has an overall configuration which approximates the arcuate configuration of a person's (upper and lower) teeth (see FIG. 2). There is an upper, inwardly disposed, generally U-shaped compartment 12, of the same arcuate extent as the overall device, which, in use, will accommodate the downwardly extending upper teeth of the wearer, and a lower similarly configured but reversely disposed compartment 14, of the same arcuate extent, to receive the upwardly extending lower teeth of the wearer. The upper and lower compartments 12, 14 are spaced and separated by a central, generally horizontally disposed member 16 which is common to both compartments (its opposite surfaces respectively constituting the base of the upper compartment, and the top of the lower compartment). Each compartment is provided throughout with a series of projecting protuberances 18, preferably 1–2 mm in diameter, which do not prevent, or are arranged to permit, the entrance of the teeth and which will be in contact with the teeth when the device is in place for use. One of the functions of the protuberances, which will be discussed further below, is to promote isotonic exercise (better blood flow) of the relevant musculature.

At its front, the device has an arcuately configured vertically disposed continuous member 22, the front surface 24 (i.e., the surface seen by the viewer when the device is in the slightly open mouth of the wearer) of which is smooth and planar and the rear surface 26 of which constitutes respective vertical surfaces of the teeth accommodating compartments. At its rear, the device is cut away to provide an inwardly extending smooth-walled cavity 28, which, in use, will accommodate the tongue of the subject. The reverse surface of the cavity is inwardly inclined and constitutes the opposite respective surfaces 30, 32 of the teeth accommodating compartments 12 and 14, respectively.

As just described, the upper and lower compartments 12, 14 are in the same vertical plane. However, these planar relationship may be varied. For example, the lower portions of the device may be constructed so as to be more anteriorly situated.

The protuberances will generally be equi-spaced and dimensioned, normally disposed to the surface from which they protrude and are arranged in parallel rows. However, this regime can be varied as required. One such instance is in the case where the method and device of the invention are employed in the course of the treatment of a patient in respect of whom diagnosis has indicated the need to move the Condylar head of the mandible forward in the Glenoid fossa. The consequence of such movement is the creation of a space between the posterior teeth, which in turn can lead to an unhealthy condition in the joint and jaw supporting tissues. To assist in such a situation, the device is constructed so that some of the protuberances, in particular the protuberances towards the ends of the upper and lower compartments (i.e., the rearwardly situated protuberances when the device is in position), are of increased width and height, a typical such increase being of the order of 50–150% (e.g., 2–3 mm, and up to 5 mm in height respectively). This will provide the contact that is necessary to maintain the health of the joint and jaw muscles during treatment.

This last-mentioned embodiment of the device, wherein appropriately located selective protuberances are selectively provided and/or differently dimensioned than the others, represents a significant feature of my invention.

To meet individual requirements (which, naturally, will vary enormously between large framed mature adults at one end of the scale, and small children at the other), the device is of course constructable in a number of sizes. It will at the same time be appreciated that the aforementioned characteristic features are common to all sizes. It is usually desirable for the upper and lower parts of the device to be in a "Dental Class 1 relationship", with a thickness of 2–3 mm of material on the biting surface. The protruding prongs on the upper outside wall of the device are preferably made shorter than on the lower thereof, due to the upper arch teeth being wider than the lower arch teeth by 2–3 mm. This, however, is subject to variation as required.

As shown in FIGS. 2 to 5, various alterations and modifications can be made to the device as hereinbefore described.

Depending upon the extent of the jaw or tooth malfunctions, further expansion or compression of the jaw or tooth may be achieved by either removing particular protrusion member, removing part or all of a portion of one or both the side walls, or providing vertical cuts in the wall portions of the compartments.

For instance, as shown in FIG. 2, a portion 40 of the front wall 24 may be cut away together with the protrusions thereon such that further expansion of the teeth is facilitated, being unrestricted by the provision of the prongs or wall 24. Whether the wall be cut away, or simply left intact and the prongs removed therefrom, will depend on the particular situation, that is, the amount of expansion required for that particular patient's jaw or teeth.

Figure 3A:
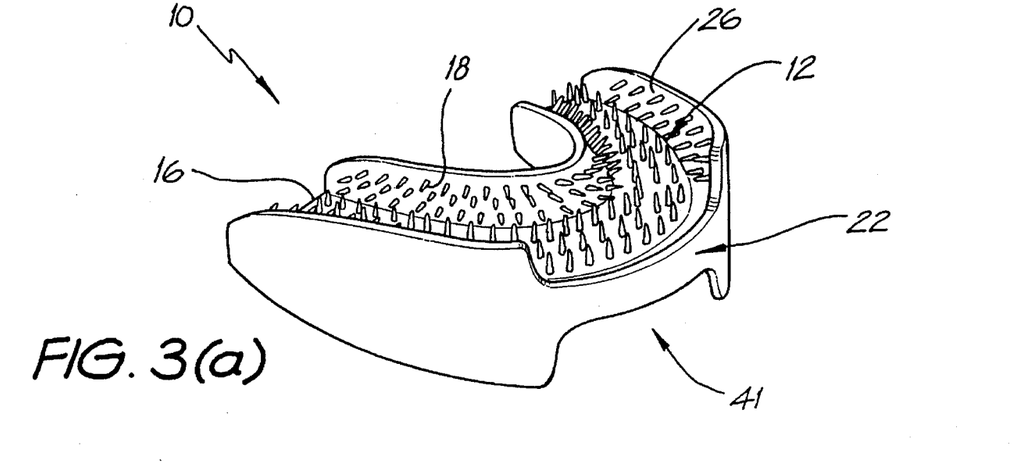
FIGS. 3(a), 3(b) and 3(c) illustrate, respectively, perspective, plan and front views of a device wherein portions of both the upper and lower side walls are cut out.
Figure 3B:
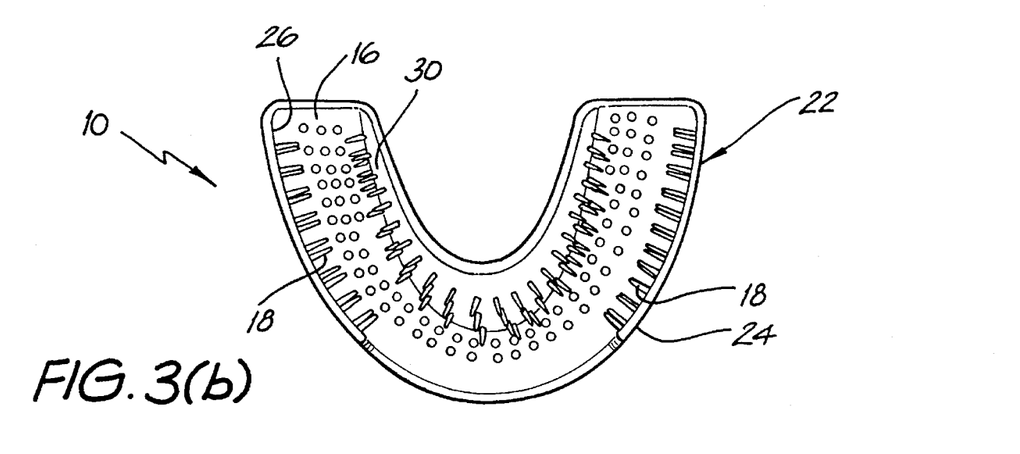
Figure 3C:
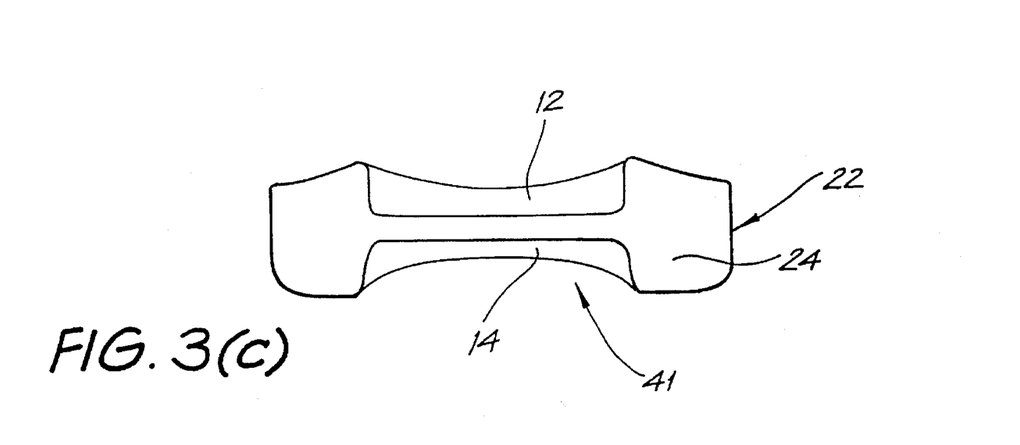

Obviously, as shown in FIG. 3, a portion 41 of the lower front wall may alternatively or additionally be removed, together with the prongs which normally protrude therefrom. Once again, the wall could alternatively be left intact, and the prongs simply removed therefrom, to allow further expansion of the teeth or jaw in that area.

Figure 4A:
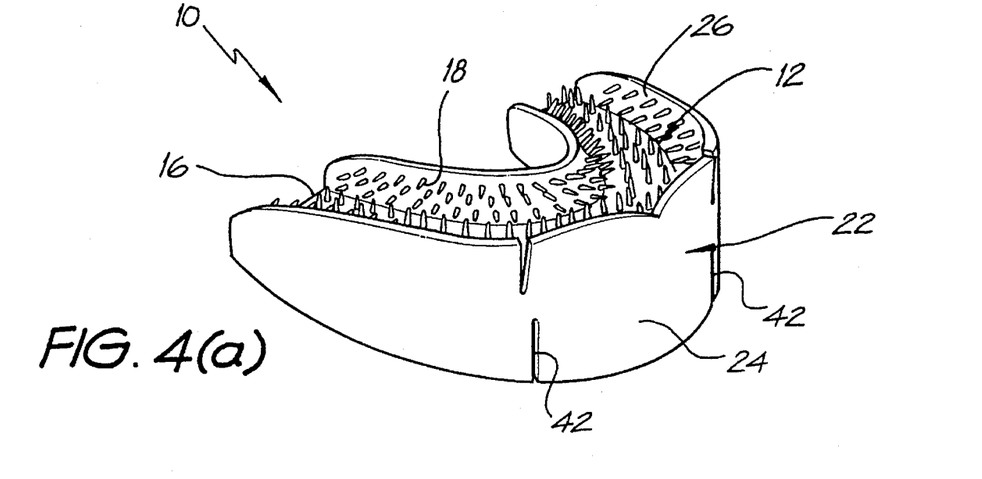
FIGS. 4(a), 4(b) and 4(c) illustrate, respectively, perspective, plan and front views of the device wherein vertical cuts are provided at selective portions of the side wall.
Figure 4B:
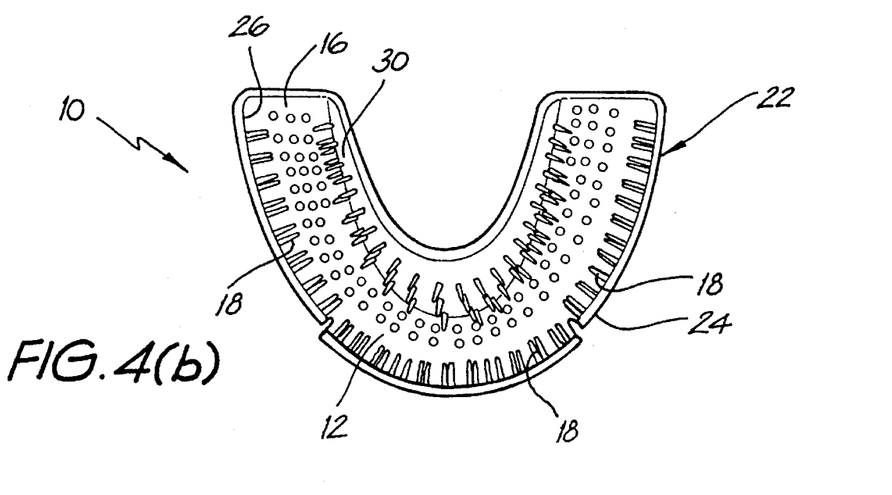
Figure 4C:
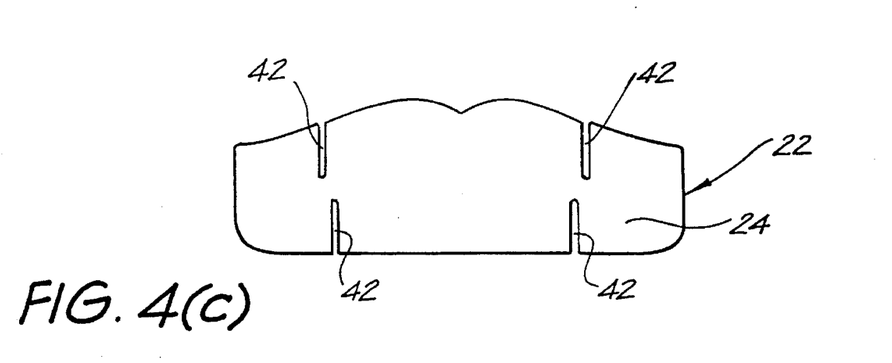

Alternatively or additionally, as shown in FIG. 4, vertical cuts 42 may be provided in the body at any appropriate portion to achieve a similar effect. In the region between the cuts 42 less rigidity will result in less pressure on the teeth from the outside prongs, which are directing forces in the direction of the tongue, allowing easier movement of the teeth or alveolar bone in that area.

Figure 5A:
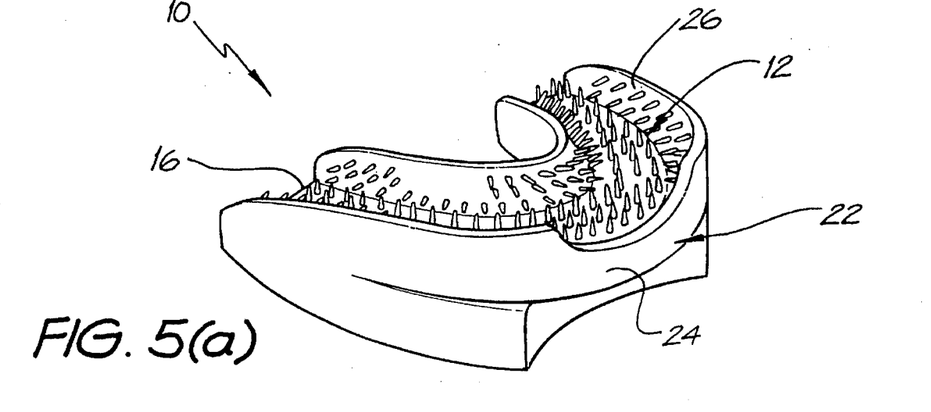
FIGS. 5(a), 5(b) and 5(c) illustrate, respectively, perspective, plan and front views of the device wherein alternative portions of the walls are cut away.
Figure 5B:
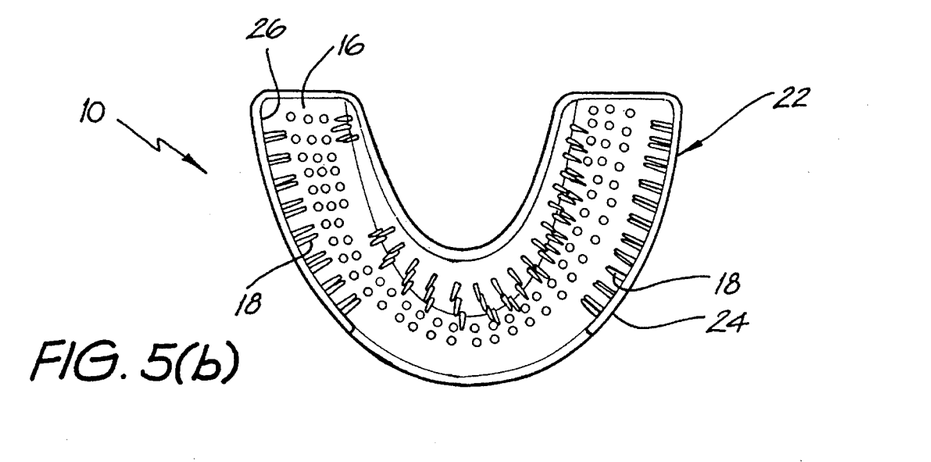
Figure 5C:
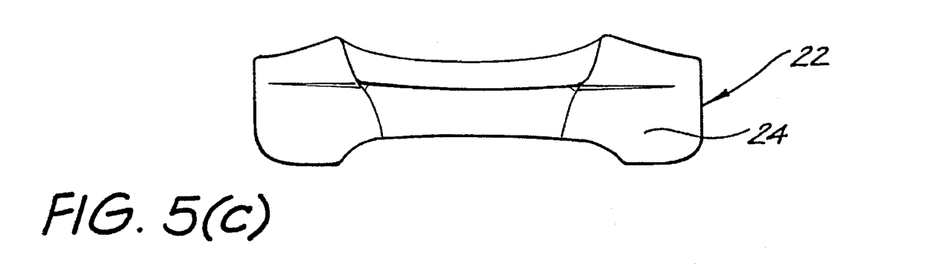

As shown in FIG. 5, the prongs may be removed from any portion within the compartment either individually, or, any portion of the compartment may be cut away.

Whilst the drawings illustrate an embodiment which generally has a pair of side walls, i.e., an outer and inner side wall, joined by a connecting wall, obviously a single wall of generally U-shape, or a V-shaped wall, may alternatively be embodied. The size and length of the protrusions are of course variable.

In use, it is envisaged that a single device would be manufactured, the design of which would be compatible to a large number of users. The device could be appropriately marked by means of sand blasting or other scribing methods to indicate to a dentist or doctor or a lay person the positions at which the device may be cut depending upon the particular requirements for different patients. The dentist or doctor can then, following determination of the extent and requirement of jaw and teeth reformation required, cut away the prongs, cut away portions of the side wall, and/or cut vertical cuts in the side walls, such that the remaining prongs then apply pressure as required to the teeth and/or jaw bone of the patient.

Whilst it is appreciated that using such a device for teeth and tooth reformation is most useful in children, adults may also use such a device for expansion/alignment of the teeth or jaws.

It has been discovered that such a device is also particularly useful as an anti-snoring device. Whilst the invention should not be bound by any particular theory of operation, the following is presented by way of a non-limiting hypothesis as to the operation of this anti-snoring device. It is considered that the bringing down of the mandible, into a downwardly forward position, following insertion of the device into the mouth of the user, facilitates airway opening in the region of the soft palate, and pharyx. This then opens the airways and maintains better oxygen tension levels in the bloodstream whilst sleeping, whilst also helping to prevent clenching and bruxing of the persons teeth whilst asleep. This alternative position of the mandible results in reduction or elimination of snoring. Obviously therefore, the wearing of this device by such persons has significant advantages, alleviating pathological conditions such as headaches, craniocervical muscle problems and temporomandibular joint problems caused by lack of sleep, bruxing of the teeth, or excess motor tone in muscles thereabouts.

It is also envisaged that the device may be used as an orthodontic retainer. After orthodontic treatment has been carried out to achieve arch expansion, there is a strong tendency for some 'release' to occur. To eliminate, or at least reduce, the amount of 'release' specialists in the field may prescribe the use of a 'retainer' to maintain the bore development, arch form, and tooth position. Consequently, the device of the present invention can be used nocturnally. If adjustments are required, these can easily be achieved by the removal of prongs on the outer wall of the device, or a portion of the walls. The device, as a retainer, has several advantages over prior art retaining devices, including the fact that it is a one piece appliance, and, that it is soft and physiologically more acceptance to the oral tissues allowing the tissues to be protected by saliva and providing some shock absorber effect to the 20% or so of children, as well as adults, who nocturnally severely grind their teeth.

Figure 6A:
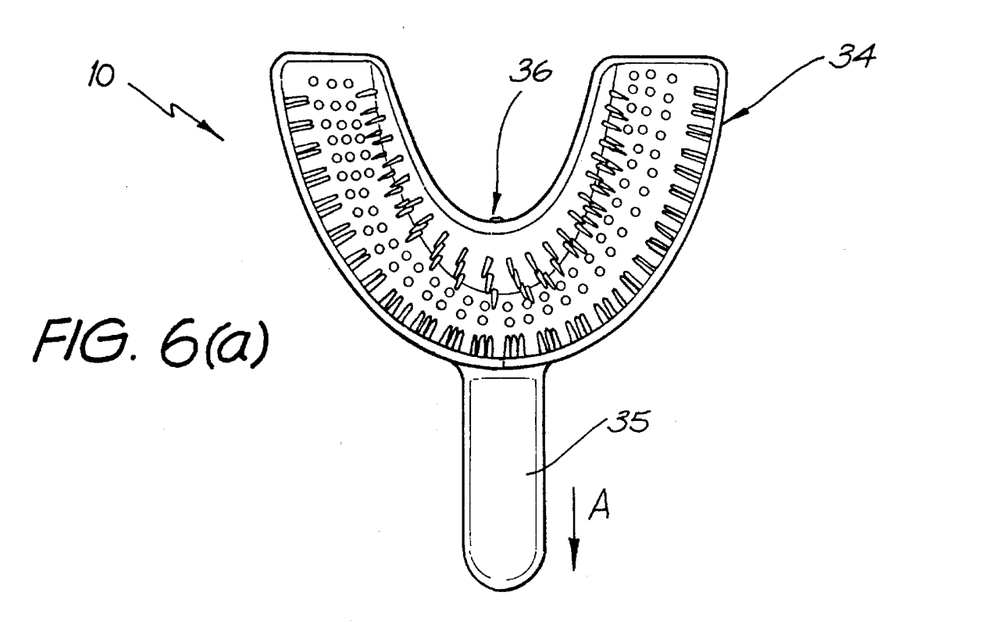
FIGS. 6(a) and 6(b) show a plan view and an elevational view, respectively, of the device of the present invention provided with a handle thereon.

A further modification to the device is shown in FIG. 6, wherein the device 10 is provided with a handle 35 attached to the main body portion 34 thereof. Such an embodiment is envisaged to be particularly suitable for infants, for improvements to the relative positions of the bones of the mid face and mandible, when it is considered appropriate to move these bones forward relative to the skull base. A child pulling on the handle in the direction shown by the arrow will assist the forward movement of the bones and/or teeth in that direction.

A raised or slightly roughened area about 2 mm diameter may be provided on the tongue side of the device to train people, particularly children about the correct position of their tongue at rest or during waking hours. Such an embodiment is shown in FIG. 6, with the tongue contact portion indicated by the numeral 36.

Figure 6B:
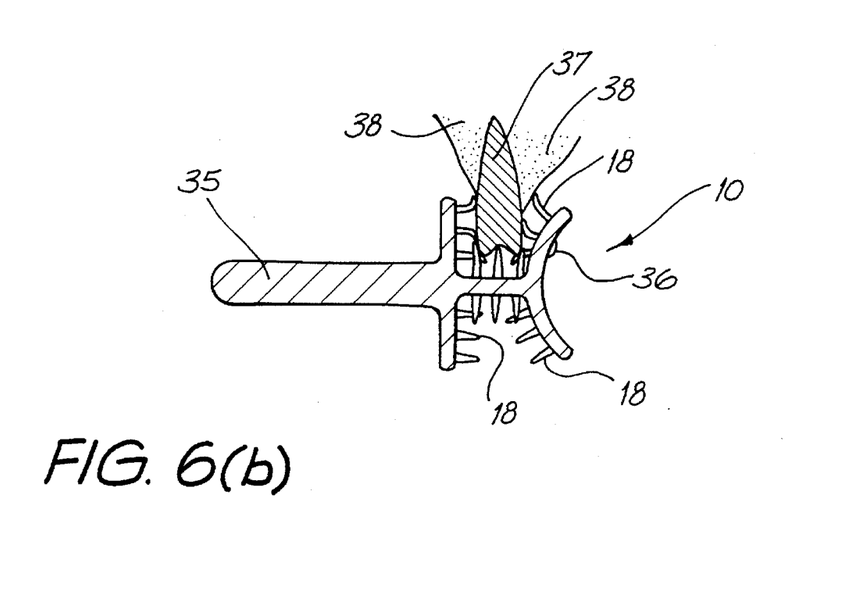

It should be noted that, in operation, the device may be chosen such that the length of the prongs 18 are bent when abutting against the teeth 37 or bone 38 of the wearer, such that the elastic forces of the prongs tend to assist in movement of the teeth or jaw. The adjacent prongs on the opposite wall, as shown in FIG. 6(b) may be provided of short length, such that they do not prevent movement of the teeth.

Where specific details are set forth in the foregoing description, such as size, particular configurations, and the like, such details are to be regarded as no more than illustrative of preferred forms of the invention. As long as the basic criteria is observed, all such non-critical matters can be varied in accordance with the situational requirements. Likewise, whilst specific functions and modes of action have been set forth, others are within the view of the overall invention.

Although preferred forms of the invention have been described for illustrative purposes, those skilled in the art would appreciate that many additions, modifications, and substitutions are possible without departing from the spirit and scope of the invention as described hereinbefore and as claimed hereinafter.

I claim:

1. A mouth worn apparatus, comprising:

a main body having upper and lower compartments which are generally U-shaped so as to conform generally to a patient's teeth, the upper compartment opening at least upwardly and the lower compartment opening at least downwardly so as to generally receive a patient's upper and lower teeth, respectively; and, a plurality of flexible protrusion members extending from at least part of the interior surface of at least one of said compartments so as to contact at least some of the patient's teeth when the device is worn, certain of said protrusion members being positioned to contact certain parts of selected teeth and being longer in comparison to those positioned to contact other of said teeth.

2. A mouth worn apparatus as claimed in claim 1, when used to achieve gradual movement of said selected teeth when said apparatus is worn by a patient.

3. A mouth worn apparatus as claimed in claim 1, wherein each said compartment comprises at least one side wall and a connecting wall, and wherein certain portions of said at least one side wall are selectively removed.

4. A mouth worn apparatus as claimed in claim 3, wherein certain portions of at least one side wall are provided with at least one vertical cut therein.

5. A mouth worn apparatus as claimed in claim 1, wherein each compartment comprises a pair of side walls and a connecting wall, and wherein certain portions of at least one side wall are selectively removed.

6. A mouth worn apparatus as claimed in claim 5, wherein certain portions of at least one side wall are provided with at least one vertical cut therein.

7. A mouth worn apparatus as claimed in claim 1, when used as an anti-snoring device.

8. A mouth worn apparatus as claimed in claim 1, when used for the prevention of clenching or bruxing of a patient's teeth.

9. A mouth worn apparatus as claimed in claim 1, when used as an orthodontic retainer.

10. A mouth worn apparatus as claimed in claim 1, further provided with a handle thereon adapted to extend outwardly of a wearer's mouth.

11. A mouth worn apparatus as claimed in claim 1, further comprising a tongue resting portion thereon to indicate/train a wearer as to a desirable resting location for the tongue.

12. A mouth worn apparatus as claimed in claim 1, wherein certain portions of said at least one side wall are selectively removed.

13. A mouth worn apparatus as claimed in claim 12, wherein certain portions of at least one side wall are provided with one or more vertical cut(s) therein.

14. A mouth worn apparatus as claimed in claim 1, wherein certain portions of at least one said wall are provided with at least one vertical cut therein.

15. A method for treating jaw and tooth malformations, said method being directed at moving one or more of a patient's teeth and making use of an apparatus having upper and lower compartments which are generally U-shaped so as to conform generally to a patient's teeth, and having a plurality of flexible protrusion members extending from at least part of the interior surface of a at least one of said compartments so as to contact at least some of the patient's teeth when the device is worn, said method comprising the steps of:

selectively cutting away portions of said protrusion members;

placing the device in the mouth of a patient so that the upper and lower teeth are substantially received in the upper and lower compartments of the device, respectively, and, retaining the device within the patient's mouth for a predetermined period of time such that any protrusion members which contact the patient's teeth apply pressure thereto whereby gradual movement of said teeth is facilitated.

16. A method for treating jaw and tooth malformations, said method being directed at moving one or more of a patient's teeth and making use of an apparatus having upper and lower compartments which are generally U-shaped so as to conform generally to a patient's teeth, and having a plurality of flexible protrusion members extending from at least part of the interior surface of at least one of said compartments so as to contact at least some of the patient's teeth when the device is worn, said method comprising the steps of:

selectively cutting away portions of the wall portions of said compartment(s);

placing the device in the mouth of a patient so that the upper and lower teeth are substantially received in the upper and lower compartments of the device, respectively, and, retaining the device within the patient's mouth for a predetermined period of time such that any protrusion members contact the patient's teeth apply pressure thereto whereby gradual movement of said teeth is facilitated.

17. A method for treating jaw and tooth malformations, and method being directed at moving one or more of a patient's teeth and making use of an apparatus having upper and lower compartments which are generally U-shaped so as to conform generally to a patient's teeth, and having a plurality of flexible protrusion members extending from at least part of the interior surface of at least one of said compartments so as to contact at least some of the patient's teeth when the device is worn, said method comprising the steps of:

providing one or more vertical cut(s) in the wall portions of said compartment(s);

placing the device in the mouth of a patient so that the upper and lower teeth are substantially received in the upper and lower compartments of the device, respectively, and, retaining the device within the patient's mouth for a predetermined period of time such that any protrusion members which contact the patient's teeth apply pressure thereto whereby gradual movement of said teeth is facilitated.

* * * * *